United States Patent [19]

Christianson et al.

[11] Patent Number: 5,171,531

[45] Date of Patent: Dec. 15, 1992

[54] APPARATUS FOR AUTOMATIC DELIVERY OF A VIAL TO AN AUTOMATED SAMPLING SYSTEM

[75] Inventors: John A. Christianson, Vancouver, Wash.; Mark R. Bateman, Mountain View, Calif.

[73] Assignee: Hewlett-Packard Company, Palo Alto, Calif.

[21] Appl. No.: 681,444

[22] Filed: Apr. 3, 1991

Related U.S. Application Data

[63] Continuation of Ser. No. 427,325, Oct. 25, 1989, abandoned.

[51] Int. Cl.⁵ .................... G01N 31/00; B01L 9/06; B01L 7/00
[52] U.S. Cl. .................... 422/64; 422/63; 422/67; 422/102; 422/104
[58] Field of Search .................... 422/62-68, 422/72-73, 101-102, 104; 436/48, 46; 435/293, 300, 301; 141/94, 144, 148; 294/64.1

[56] References Cited

U.S. PATENT DOCUMENTS

| | | | |
|---|---|---|---|
| 3,841,687 | 10/1974 | Banyas et al. | 294/64.1 |
| 4,200,607 | 4/1980 | Suzuki | 422/64 |
| 4,478,095 | 10/1984 | Bradley et al. | 422/67 |
| 4,494,583 | 1/1985 | Reeves, Jr. et al. | 141/94 |
| 4,539,296 | 9/1985 | Manabe | 422/64 |
| 4,595,562 | 6/1985 | Liston et al. | 422/64 |
| 4,615,866 | 10/1986 | Hyde et al. | 422/106 |
| 4,650,233 | 3/1987 | Mang et al. | 294/64.1 |
| 4,656,007 | 4/1987 | Douchy et al. | 422/63 |
| 4,662,668 | 5/1987 | Hufford | 294/64.1 |
| 4,699,767 | 10/1987 | Aihara | 422/65 |
| 4,713,974 | 12/1987 | Stone | 422/81 |
| 4,774,055 | 9/1988 | Wakatake et al. | 422/73 |
| 4,795,710 | 1/1989 | Muszak et al. | 422/64 |
| 4,824,641 | 4/1989 | Williams | 422/73 |
| 4,865,810 | 9/1989 | Simon | 422/72 |

*Primary Examiner*—James C. Housel
*Assistant Examiner*—Jan M. Ludlow

[57] ABSTRACT

An apparatus and method for selecting a vial from a plurality of vials and for transporting the selected vial to a sampling device such as a capillary zone electrophoresis apparatus. The apparatus comprises a removable turret assembly for holding a plurality of vials, a drive for rotating the turret assembly and for aligning a selected vial with the sampling device, and a transport device for transporting the selected vial to the sampling device. The appratus may further comprise a device to supply a cooled gas to the turret assembly, and a control device for controlling the drive and the transport device.

10 Claims, 5 Drawing Sheets

APPARATUS FOR AUTOMATIC DELIVERY OF A VIAL TO AN AUTOMATED SAMPLING SYSTEM

CROSS REFERENCE TO RELATED APPLICATION

This is a continuation of copending applications Ser. No. 07/427,325 filed Oct. 25, 1989, now abandoned.

FIELD OF THE INVENTION

The present invention relates to a novel apparatus and method for automating sampling procedures wherein the material to be sampled is in a sample container such as a vial or test tube. For simplicity, the sample container will hereinafter be referred to as a vial. The invention is especially useful for automating Capillary Zone Electrophoresis.

BACKGROUND OF THE INVENTION

Electrophoresis is the separation of molecules in a fluid or gel using an electromotive force. Capillary zone electrophoresis (CZE) is a specific type of electrophoresis which takes place in a capillary tube. The tube is filled with a conductive fluid, i.e., an electrolyte or buffer. A small amount of the sample to be separated is then introduced into one end of the capillary. A high-voltage, for example 30,000 volts, applied across the electrolyte at the ends of the capillary tube supplies the electromotive force required to separate the sample into its constituent molecules. Once separation of the molecules occurs, an optical detector may then be used to "look" through the tube at the exiting end to see the results of the separation.

A major drawback to CZE is the complexity of the process. The process requires: filling the capillary tube with a buffer or electrolyte, introducing a sample to be separated into one end of the tube, providing an electrical connection to the electrolyte at each end of the tube, providing the required high-voltage across the electrical connection made at each end of the tube, and viewing the results through the tube. Each of these steps is a manual process which requires a trained technician to perform. After preparing the contents of the tube and starting the electrophoresis operation, the technician must then wait until the electrophoresis is complete before stopping the operation and rinsing the capillary tube in preparation for the next operation. It is towards automating the CZE process and other sampling processes, and thereby, reducing the amount of operator intervention required, that the present invention has been developed.

SUMMARY OF THE INVENTION

The invention is directed to an apparatus and method for selecting a vial from a plurality of vials and for transporting the selected vial to a sampling device such as a capillary zone electrophoresis apparatus. The apparatus comprises a removable turret assembly for holding a plurality of vials, a drive means for rotating the turret assembly and for aligning a selected vial with a sampling means, and a transport means for transporting the selected vial to the sampling means.

The turret assembly comprises a pair of shells and a plurality of elongated vial sleeves. The two shells and the elongated vial sleeves are fitted together to form a plurality of vial holding assemblies therein.

The invention further comprises a hub assembly upon which the turret assembly is mounted. The turret assembly may be easily removed from the hub assembly for loading or replacement with another turret assembly. The hub assembly allows the turret assembly to be rotated on a central shaft. The hub is rotated by drive means comprising a stepper motor. The hub assembly also provides passage for a cooled gas to the turret assembly.

The transport means comprises a motor with a conversion means for translating rotational motion of the motor into a linear transport motion.

This invention further comprises a control means for controlling vial selection and delivery by controlling the rotation of the turret assembly and the transportation of a selected vial. The control means comprises an initialization means for corresponding the rotational position of the turret assembly to a given vial, an instruction set comprising an order in which the vials are to be transported to the sampling means, and a digital processor.

The control means further comprises a sensing mechanism which detects when the vial is secured to the sampling apparatus for processing.

Additional features and advantages of this invention will become apparent from the detailed description and accompanying drawings of the preferred embodiment which follow.

Figure 1:
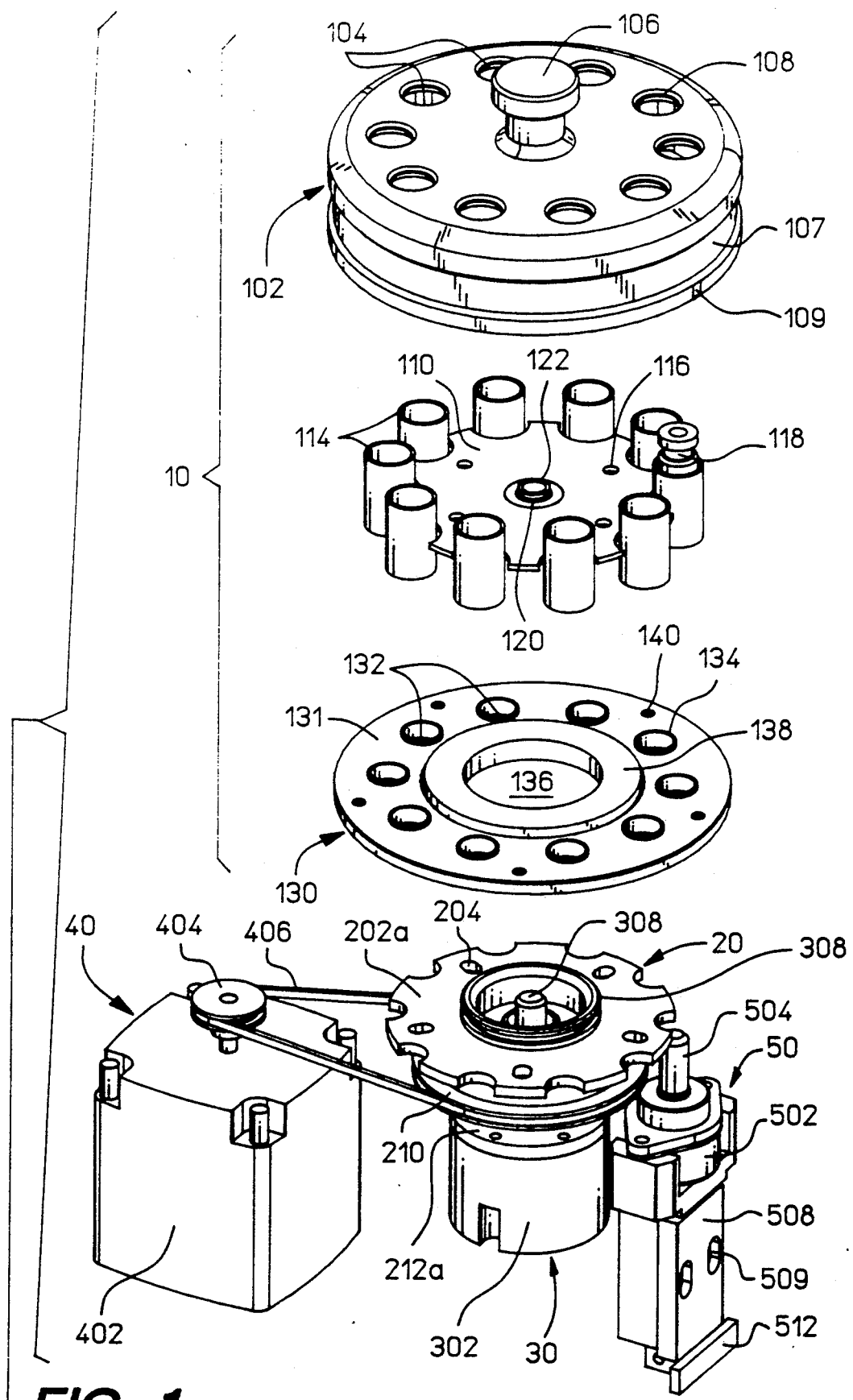
FIG. 1 shows an exploded view of the turret assembly and the turret drive assembly of the present invention.
Figure 2A:
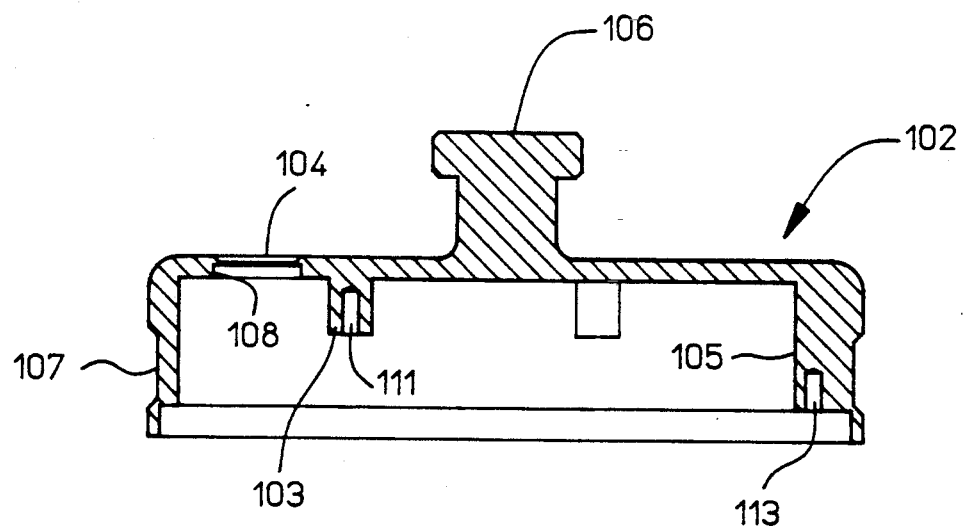
FIG. 2a shows a cross-section of the first shell of the turret assembly.
Figure 2B:
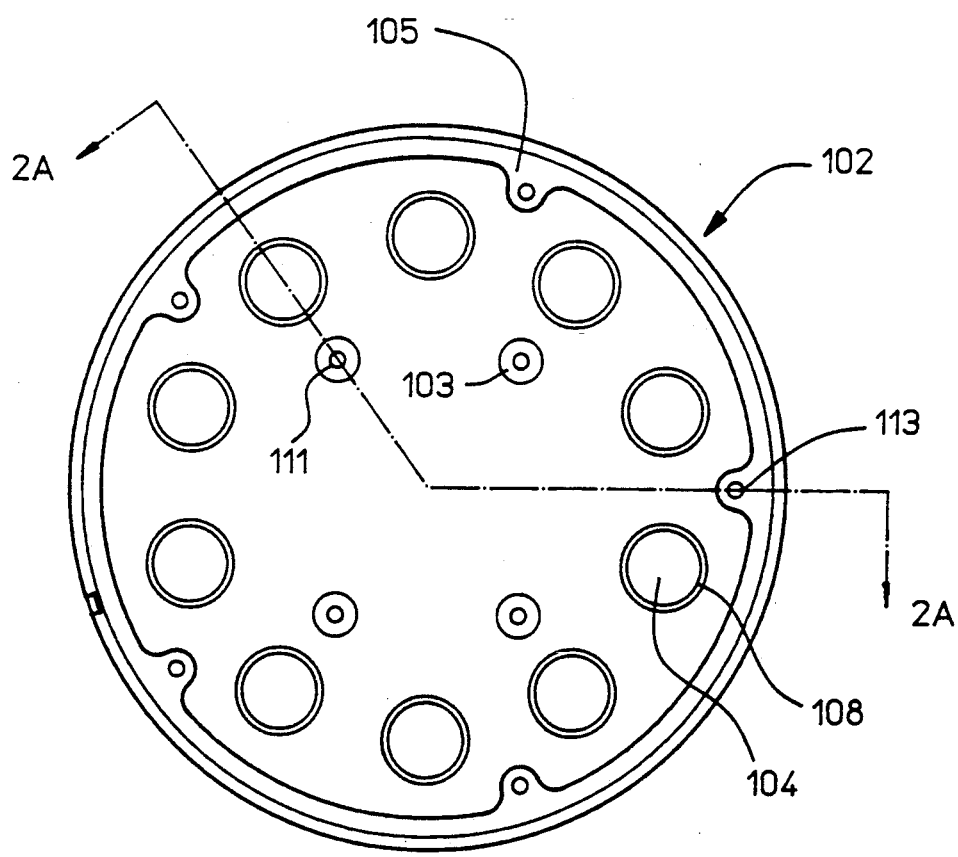
FIG. 2b shows a perspective view of the inner portion of the first shell of the turret assembly.
Figure 3A:
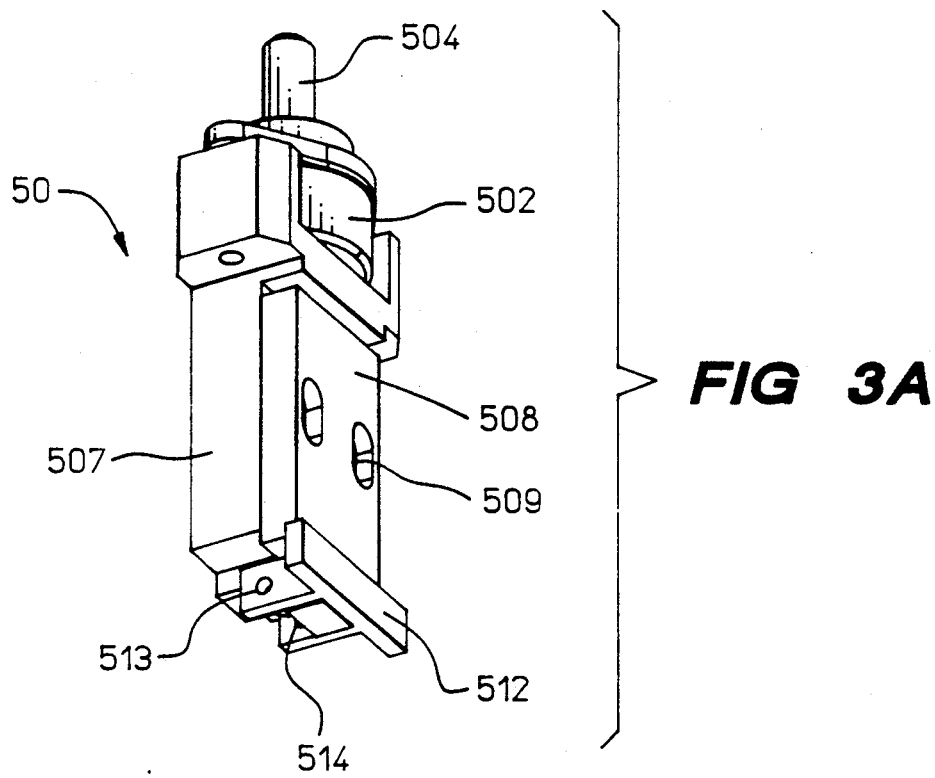
FIGS. 3a and 3b show opposite side views of the vial transport assembly.
Figure 3B:
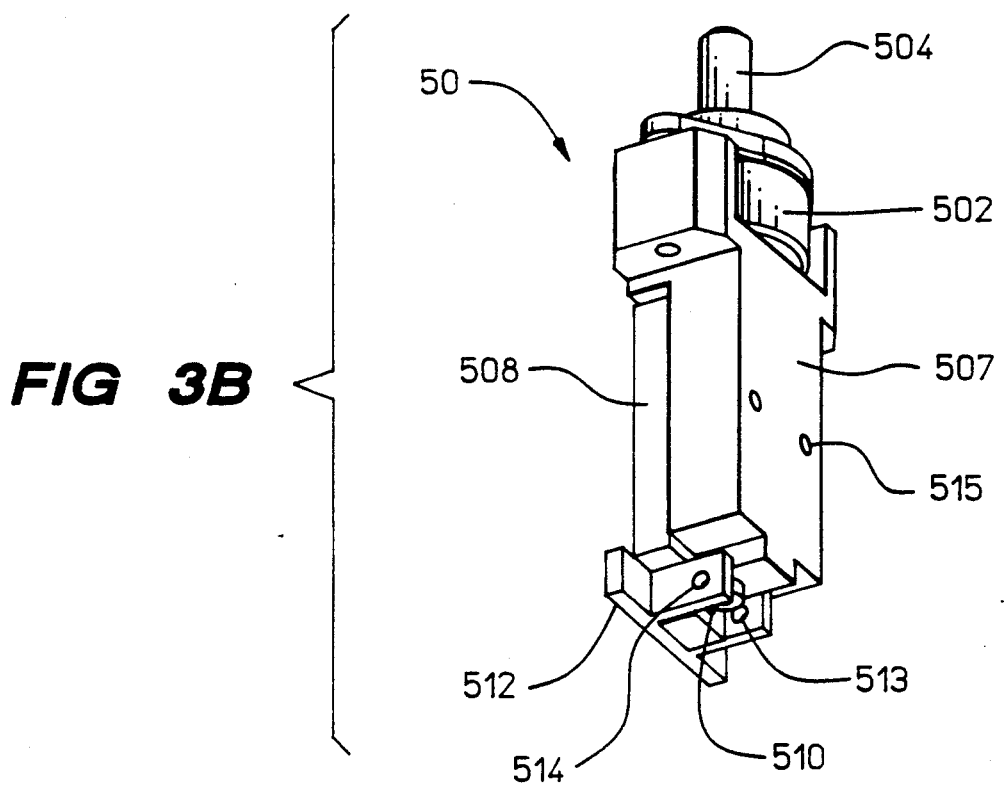

In the figures, it should be understood that like reference designators represent like components.

DETAILED DESCRIPTION OF THE PREFERRED EMBODIMENT OF THE INVENTION

Referring now to FIGS. 1-4, a detailed description of the preferred embodiment of the invention is presented.

Overview

The apparatus of the present invention allows the automation of CZE, and other sampling processes, since it can deliver a series of vials containing electrolytes, samples, rinses or other solutions to a CZE apparatus or other sampling device per the instruction of a controller without manual assistance or supervision. The apparatus further provides cooling for the vials. This feature is especially desirable where biological samples, which can degrade after extended exposure to room temperature, are used.

Turret Assembly 10

A turret assembly 10 comprises a first shell 102, a second shell 130, and disposed therebetween, a number of elongated vial sleeves 114 and a baffle 110. First shell 102 has a dome shape with a lifting knob 106 extending outward from the center of turret assembly 10. A number of openings 104 are arranged in a circular pattern about the periphery of first shell 102. Each opening 104 has a counter-bore 108 disposed at its periphery on the inner portion of first shell 102. A reflective mark 109 is disposed on the outer surface of first shell 102 on a skirt portion 107.

Second shell 130 is disk shaped and has a plurality of openings 132 which correspond in position to the openings 104 in first shell 102. Openings 132 are smaller in diameter than openings 104 such that a sample vial 118 may pass through opening 104 but not opening 132. Each opening 132 has a raised boss 134 at its periphery extending into the inner portion of turret assembly 10. A circular central opening 136, in second shell 130, has a raised boss 138 at its circumference extending into the inner portion of the turret assembly 10. A number of screw holes 140 are set symmetrically around the circumference of second shell 130. A rubber gasket 131 is formed to have openings to correspond to bosses 134, 138 and to holes 140.

Second shell 130 is fixedly secured to first shell 102 by means of screws or similar fasteners inserted through holes 140 in second shell 130 and into a number of mating screw holes 113 in first shell 102. Each mating screw hole is formed in a raised boss 105 disposed on the inner surface of skirt portion 107 of first shell 102. A corresponding raised boss 105 with mating screw hole 113 is aligned with each of holes 140 when shells 102 and 130 are joined together as described hereinbelow.

Shells 102 and 130 are aligned, before securing them together, such that openings 104 in first shell 102 coincide with openings 132 in second shell 130 and such that each elongated vial sleeve 114 is aligned to coincide with an opening 104 at a first end and an opening 132 at a second end to form a vial holding assembly 150 therebetween. Each elongated file sleeve 114 is of an inner diameter substantially equal to the outer diameter of the raised bosses 134, and of an outer diameter substantially equal to the inner diameter of counter-bore 108.

Each vial sleeve 114 is aligned to coincide with counter-bore 108 on first shell 102 and raised boss 134 on second shell 130. When shells 102 and 130 are secured together, first end of vial sleeve 114 is inserted into counter-bore 108 and boss 134 is inserted into second end of vial sleeve 114. In this manner, vial sleeve 114 is secured in place between shells 102 and 130 to form vial holding assembly 150. A turret chamber 142 is formed between shells 102 and 130 as part of a circulation passage for a cooled gas as described in more detail below.

It is preferred that vial sleeves 114 be formed from a thermally conductive material. This will aid in the transfer of heat from sample vial 118, disposed within vial holding assembly 150, to a cooled gas flowing through turret chamber 142. On the other hand, it is desirable to form upper shell 102 and lower shell 130 from a thermally insulating material in order to reduce heat transfer through shells 102 and 130. It is also desirable that both materials be electrically non-conductive to minimize the amount of conductive material in proximity to the high voltage potentials used in CZE. An insulating plastic material would be suitable for shells 102 and 130. A plastic material with greater thermal conductivity should be used for vial sleeves 114.

A disk-shaped baffle 110 is disposed within turret chamber 142. Four holes 116 are arranged in a circular pattern on baffle 110. Baffle 110 is secured within first shell 102 by means of screws or similar fasteners. Each screw extends through hole 116 in baffle 110 into a mating hole 111 in a raised boss 103 formed on the inner surface of first shell 102. A centrally located opening 120 passes through baffle 110. A slider tube 122 having an outer diameter substantially equal to the inner diameter of opening 120 passes therethrough.

Hub Assembly 20

A hub 202 and a spindle 212 are generally referred to as hub assembly 20. Hub 202 has, at one end, a substantially flat mounting plate 202a upon which turret assembly 10 is mountable. A pulley 210 is attached on the outer circumference of hub 202. When turret assembly 10 is mounted on mounting plate 202a, a raised boss 208 is inserted into central circular opening 136 of second shell 130. An o-ring 214 provides a seal between these mating surfaces. A number of locating dowels 148, extending from second shell 130, are inserted into a number of holes 204 in mounting plate 202a to secure turret assembly 10 from rotation independent of hub 202. Spindle 212, having a base portion 212a and a central bore 206 passing longitudinally therethrough, is inserted into a hollow cylindrical bore of hub 202 such that hub 202 may spin freely on spindle 212 while resting on base portion 212a. A snap ring 218 prevents the hub 202 from being removed from the spindle 212.

Turret Cooling System 30

Figure 4:
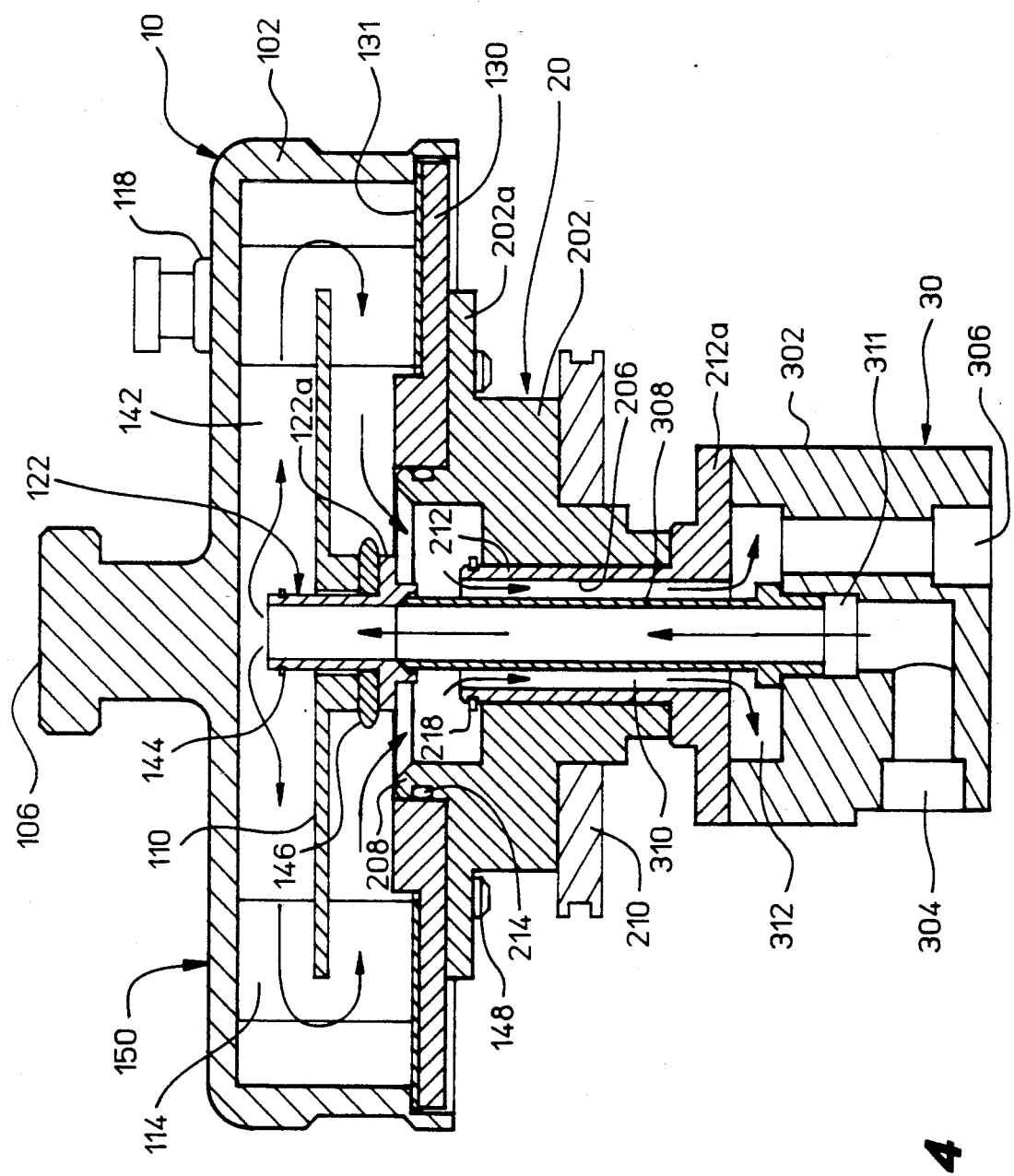
FIG. 4 shows a cross-section of the turret assembly, the hub assembly and the turret cooling system.
Figure 5:
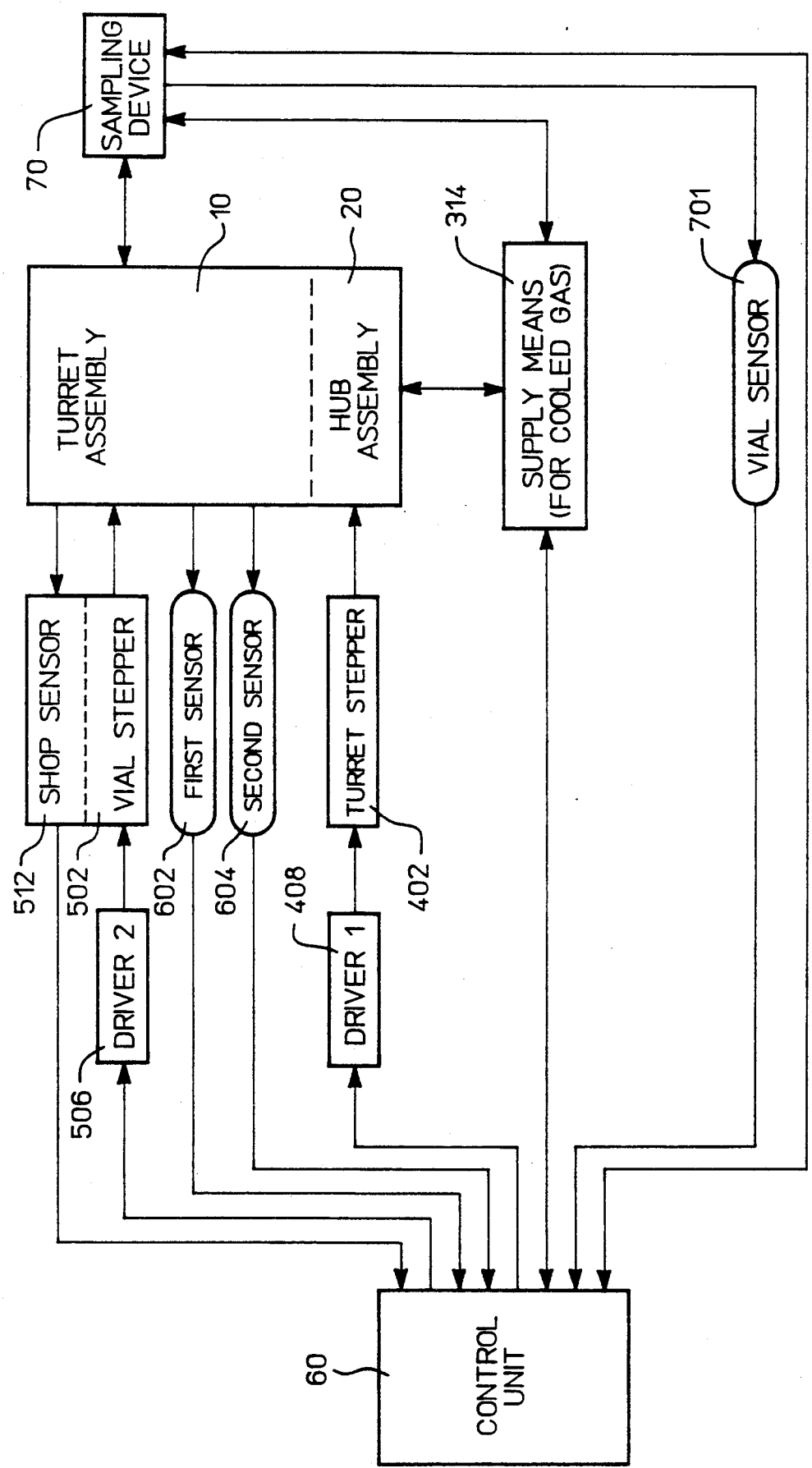
FIG. 5 shows a block diagram of the present invention.

It is the function of the turret cooling system 30 to provide for passage and circulation of a cooled gas to cool sample vials 118 in vial holding assemblies 150. A supply means 314, of a kind commonly known for cooling a gas, supplies the cooled gas to the turret cooling system 30. Supply means 314 may also supply the cooled gas to a sampling device 70. The supply means 314 is represented in FIG. 4 only.

The turret cooling system 30 comprises a cooling manifold 302 and an inlet tube 308 which act in conjunction with elements of turret assembly 10 and of hub assembly 20. Inlet tube 308 has an outer diameter substantially smaller than the inner diameter of central bore 206 of spindle 212. Inlet tube 308 is disposed within central bore 206 of spindle 212 and extends outward from each end of central bore 206. Inlet tube 308 has a first end which extends outward from hub assembly 20 a distance substantially equal to the elevation of raised boss 208 above hub assembly 20 and a second end which extends outward from base 212a of spindle 212. A chamber 310 is formed between inlet tube 308 and central bore 206.

Slider tube 122 of turret assembly 10 has a beveled surface at one end which mates with an oppositely beveled surface at the first end of inlet tube 308 to provide a substantially leak-free passage through which the cooled gas may flow. An o-ring type assembly, preferably a foam donut, 146 acts as a spring mechanism to force slider tube 122 down onto inlet tube 308, further enhancing that seal. Additionally, foam donut 146 provides a seal between a base portion 122a of slider tube 122 and baffle 110, thereby preventing the cooled gas from flowing between slider tube 122 and central opening 120. A snap ring 144 prevents slider tube 122 from removal from turret assembly 10 when turret assembly 10 is lifted free from mounting plate 202a. The second end of inlet tube 308 extends outward from base 212a of spindle 212 and into a seat 311 disposed within cooling manifold 302.

A cooled gas such as air or nitrogen is introduced to cooling manifold 302 at an inlet 304. The cooled gas flows through inlet tube 308 to slider tube 122. The cooled gas then flows through slider tube 122 into turret chamber 142 where it is directed by baffle 110 past each of vial sleeves 114 such that each vial sleeve 114 is cooled. Given a sample vial 118 in vial holding assembly 150, cooling each vial sleeve 108 will result in a cooling of the air trapped between sample vial 118 and vial sleeve 114. This in turn cools sample vial 118 and its contents.

The gas, having absorbed heat energy from the vial sleeves 114, then flows down through chamber 310 formed between inlet tube 308 and central bore 206 to a collection chamber 312 of cooling manifold 302. Cooling manifold 302 then directs the gas out of an exhaust 306.

Gasket 131, foam donut 146, counter-bores 108, raised bosses 134 and o-ring 214 act to maintain turret chamber 142 as a substantially leak-free passageway. Thereby, the cooled gas flowing across vial sleeves 114 may be recirculated through a closed cooling system to improve cooling efficiency and reduce energy loss.

Turret Drive Assembly 40

A turret stepper 402, a pulley 404 and a drive belt 406 are generally referred to as turret drive assembly 40. Turret stepper 402 is a known stepper motor of common design. Turret stepper 402 drives pulley 404 which in turn rotates hub 202 and turret assembly 10 on spindle 212 via drive belt 406 which is engaged with pulley 210 of hub 202. Turret stepper 402 is driven by a driver 408.

In the preferred embodiment, turret stepper 402 is a Hurst Manufacturing Instrument-Grade Stepping Motor, Model No. 3804-001. Driver 408 is a Hurst PC Board Assembly, Model No. EPC-013.

Vial Transport Assembly 50

Vial transport assembly 50 comprises a vial stepper 502, a shaft 504, a base 507, a mounting plate 508, and a shaft sensor 512.

Vial stepper 502 is a known stepper motor of common design with a means for translating rotational motion to linear motion. One common method of performing this transformation is to have a shaft threaded on its surface with screw threads and a rotating bobbin which has screw threads in its inner bore to correspond to the threads of the shaft which passes therethrough. By preventing the shaft from rotation while rotating the bobbin, a longitudinal motion of the shaft can be achieved.

When turret assembly 10 is not rotating, vial stepper 502 may drive shaft 504 up through opening 132 in second shell 130, thereby, contacting sample vial 118 and lifting that vial up through opening 104 in first shell 102 to sampling device 70 which may be a CZE apparatus. Vial stepper 502 is driven by a driver 506.

Vial stepper 502 is a known transport means. In the preferred embodiment, vial stepper 502 is an Airpax Digital Linear Actuator Model No. L92141-P2. Driver 506 is an Airpax Model SAAI027 Stepper Motor 1C Driver. It shall be obvious to those skilled in the art that other devices are known and could be used for vial stepper 502.

Shaft sensor 512 is fixedly secured to mounting plate 508 by means of a screw or similar fastener inserted through hole 510 in mounting plate 508 and into a mating hole (not shown) in shaft sensor 512. The shaft sensor 512/mounting plate 508 assembly is fixedly secured to base 507 by means of screws or similar fasteners inserted through holes 509 in mounting plate 508 and into mating holes 515 in base 507. The oblong shaping of holes 509 in mounting plate 508 allow the vertical adjustment of the shaft sensor 512/mounting plate 508 assembly relative to base 507.

Control Unit 60

A control unit 60 controls the operation of turret stepper 402, vial stepper 502, sampling device 70, and may also control supply means 314 which supplies the cooled gas to turret cooling system 30. Control unit 60 is a digital processor capable of storing a set of instructions, executing them sequentially and storing data input from sampling device 70. The preferred embodiment of control unit 60 is a Hewlett Packard Vectra MS-DOS based personal computer.

Operation of the Invention

Operation of the preferred embodiment of the present invention is now described with reference to FIGS. 1–4.

A number of vials 118 are loaded into vial holding assemblies 150 of turret assembly 10. An instruction set, which includes data pertaining to the contents of each vial and their corresponding position in turret assembly 10, is loaded into control unit 60. Turret assembly 10 is mounted on mounting plate 202a of hub assembly 20. An initialization is then performed to orient the position of turret assembly 10 to a home position. Once home position is determined, the controller can calculate an angle step required to reach any vial holding assembly 150. For example, a turret assembly with ten vial holding assemblies would have thirty-six degrees rotation between consecutive vial holding assembly positions.

The initialization is performed by two optical sensor units. A first sensor 602 determines whether the turret assembly 10 is mounted on the mounting plate 202a of the hub 202. First sensor 602 comprises a light emitting diode (LED) and a photo-receptor. The receptor is located at a point remote from the LED such that the light path between the two passes across a chord of the turret assembly 10 above hub assembly 20. When turret assembly 10 is mounted on mounting plate 202a, the light path between the LED and the receptor is obstructed by turret assembly 10 such that the receptor does not receive the light being emitted by the LED. Control unit 60 may then provide an interlock, based on this signal from first sensor 602, to prevent operation of turret stepper 402 and vial stepper 502 when turret assembly 10 is not mounted on mounting plate 202a.

Second optical sensor 604 comprises an LED and a photo-receptor in close proximity to one another. The LED is oriented to direct its beam of light onto turret assembly 10. Reflective mark 109 is disposed on first shell 102 of turret assembly 10. In the preferred embodiment, mark 109 is a piece of white adhesive tape disposed within a small recess or indentation on the outer surface of skirt portion 107 of first shell 102. Mark 109 corresponds to home or initial position of rotation for turret assembly 10. When initialization is commenced by the control unit 60, turret stepper 402 rotates turret assembly 10 until second sensor 604 detects a reflection from mark 109. Upon detection of the presence of mark 109 by second sensor 604, control unit 60 stops rotation of turret assembly 10 and initialization is complete.

The initialization process, and in fact all activity requiring the rotational movement of turret assembly 10, involves shaft sensor 512 in vial transport assembly 50. Shaft sensor 512 comprises an LED 513 and a photoreceptor 514, where LED 513 directs its light beam at photoreceptor 514. When shaft 504 is in the up position, photoreceptor 514 receives the light beam from LED 513 and an interlock is engaged, whereby rotational movement of turret assembly 10 is prohibited. When shaft 504 is in the down position, the light beam from LED 513 to photoreceptor 514 is broken and the interlock is disengaged, whereby rotational movement of turret assembly 10 is allowed. Thus, activities requiring the rotational movement of turret assembly 10, such as the initialization process, are suspended until shaft sensor 512 detects that shaft 504 is in the down position. The down position of shaft 504, defined as the point at which shaft 504 breaks the light beam from LED 513 to photoreceptor 514, may be adjusted by modifying the vertical position of the shaft sensor 512/mounting plate 508 assembly relative to base 507.

Once initialization is complete, control unit 60 may select any one of vials 118 in turret assembly 10 by commanding turret stepper 402 to rotate hub 202 an angular displacement measured from the initial position. Continuing the example from above of thirty-six degrees between consecutive vial holding positions, an instruction in the instruction set to step to the vial in position five (from home, position one) would involve a step of one hundred forty-four degrees.

Once selected vial 118 has been moved into position, coincident with shaft 504 of vial stepper 502, control unit 60 may instruct vial stepper 502 to raise vial 118 out of vial holding assembly 150 to sampling device 70. Sensing mechanism 701 will detect when vial 118 is secured to sampling device 70 for processing. In the preferred embodiment, sampling device 70 will be a CZE apparatus. Thereafter, control unit 60 may instruct sampling device 70 to perform the desired operation on the sample within vial 118. Once the sampling operation is complete, control unit 60 may instruct vial stepper 502 to lower selected vial 115 back into vial holding assembly 150 in turret assembly 10. Thereafter, the operation may be repeated.

Turret cooling system 30 delivers a cooled gas to turret assembly 10 in order to cool vials 118 while in the vial holding assemblies 150.

Operation in the Context of CZE

In the context of CZE, a representative operation involving the present invention would comprise the following steps. A first vial 118 containing a buffer or electrolyte is lifted so that an electrode and the end of a capillary tube are extended down into first vial 118 from a CZE apparatus. Thereupon, a portion of the electrolyte is drawn into the capillary tube by a known means such as a suction on the other end of the capillary tube, or in the case that a buffer already exists in the capillary, an electromotive force may be used to draw in further electrolyte.

Control unit 60 may then select a second vial 118 containing the sample of material to be separated. Upon selection of second vial 118 and lifting to the CZE apparatus, a sample of the material to be separated is drawn into the capillary tube by a known means such as either of the means discussed above. Control unit 60 will then select and retrieve first vial 118 containing the electrolyte. First vial 118 is raised to the CZE apparatus.

Once the end of the electrode and the capillary tube extend into the electrolyte of first vial 118, the electrolyte in the vial completes an electrical connection between the electrolyte in the capillary tube and the electrode. A similar connection can be made at the other end of the capillary tube within the CZE apparatus. The electrophoresis is then performed to separate the sample.

Upon completion of the electrophoresis, a third vial 118 containing a rinsing solution may be selected and raised to the CZE apparatus for performing a rinsing operation to purge the capillary tube in preparation for a second CZE operation.

Given a fully loaded turret assembly 10, several CZE operations can be executed automatically, one after the other, without the need for human intervention. Control unit 60, working in conjunction with the CZE apparatus or other sampling device 70, can record any data taken in the sampling operation. If it is desired to perform more CZE operations than can be accommodated by one turret assembly 10, then a robot arm may be used to empty and reload the turret assembly 10 with vials 118 stored in a substantially larger storage turret. Alternatively, the robot arm could simply replace the loaded turret assembly 10 with a second loaded turret assembly 10 retrieved from cooled storage.

Hereby, a time saving and efficient method and apparatus have been developed for the automation of CZE and other sampling processes.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced herein.

What is claimed is:

1. An apparatus for selecting a vial from a plurality of vials and for transporting the selected vial to a sampling means, the apparatus comprising:
   (a) a removable turret assembly for holding a plurality of vials, said turret assembly including:
      (i) a first shell with a plurality of first openings arranged in a substantially circular pattern around a first central axis, said first openings being of a size sufficient for a vial to pass therethrough,
      (ii) a second shell with a plurality of second openings arranged in a substantially circular pattern around a second central axis, each of said plurality of second openings being of a size insufficient for a vial to pass therethrough but large enough to permit passage of a transport means therethrough;
      (iii) a plurality of elongated vial sleeves, and
      (iv) means for securing said first and second shells to each other and to said vial sleeves such that said first axis and said second axis are coincident, and such that each vial sleeve is aligned with a first opening in said first shell and a second opening in said second shell to form a plurality of holding assemblies for the plurality of vials;
   (b) a hub assembly having a hub and a spindle, said spindle having a third axis, said hub having a first surface and a second surface, said first surface being adapted to removably mount said turret assembly thereon such that said first and second axes are substantially coincident with said third axis, and said second surface being rotatably coupled to said spindle to allow rotation of said hub about said third axis;

(c) drive means for rotating said hub assembly;

(d) transport means for removing a selected vial from said turret assembly and for transporting said selected vial to the sampling means; and (e) means for cooling the plurality of vials in said turret assembly, said means for cooling including:
  (i) a substantially circular third opening in said second shell, said third opening being substantially centered on said second axis;
  (ii) a disk shaped baffle centrally disposed within said turret assembly, said baffle being disposed substantially perpendicular to said corresponding first and second central axes;
  (iii) a fourth opening centrally located in said baffle and centered on said coincident first and second central axes;
  (iv) a slider tube having a first end inserted through said fourth opening in said baffle and a second end having a base portion, said slider tube having an outer diameter substantially the same as the diameter of said fourth opening to allow said slider tube substantially free movement within said fourth opening, said first end having a groove disposed on its outer surface to accept a snap ring to retain the slider tube in said fourth opening;
  (v) a central bore passing through said spindle of said hub assembly, said central bore being coincident with said third axis;
  (vi) an inlet tube disposed within said central bore in said spindle, said inlet tube being coincident with said third axis and having an outer diameter substantially smaller than said central bore in said spindle such that a concentric space is defined between said inlet tube and said central bore, a first end of said inlet tube extending beyond said spindle and being adapted to mate with said base portion of said slider tube through said third opening in said second shell when said turret assembly is mated with said hub; and
  (vii) a cooling manifold coupled with said spindle to provide a path for the flow of a cooling medium to a second end of said inlet tube and a return flow path for said cooling medium through said concentric space between said inlet tube and said central bore of said spindle.

2. The apparatus of claim 1, wherein said transport means further comprises:
  (i) a shaft having an extended position and an unextended position, for removing the selected vial from said turret assembly and for transporting the selected vial to the sampling means when said shaft is in said extended position;
  (ii) a vial stepper motor; and
  (iii) means for translating rotational motion of said vial stepper motor to linear motion, said means for translating coupled to said shaft for mechanically moving said shaft to said extended position and for mechanically moving said shaft to said unextended position.

3. The apparatus of claim 2, wherein said transport means further comprises:
  (iv) a base coupled to said shaft and to said vial stepper motor;
  (v) a mounting plate coupled to said base; and
  (vi) a shaft sensor coupled to said mounting plate, for detecting when said shaft is in said extended position and when said shaft is in said unextended position.

4. The apparatus of claim 1, wherein said means for cooling further comprises:
  (viii) a foam donut disposed between said base portion of said slider tube and said baffle.

5. The apparatus of claim 1, further comprising:
  (f) means for controlling said vial selection by controlling said drive means and said transport means, said means for controlling including:
    (i) means for corresponding the rotational position of said turret assembly to a selected vial; and
    (ii) an instruction sequence comprising an order in which said vials are to be transported to the sampling means.

6. The apparatus of claim 5, wherein said means for controlling is a digital processor.

7. The apparatus of claim 6, further comprising:
  (g) means for corresponding the rotation position of said turret assembly to said order of vial transportation in said instruction set.

8. The apparatus of claim 7, further comprising:
  (h) means for determining when said turret assembly is mounted on said hub.

9. A removable turret assembly for holding a plurality of vials in an automated vial delivery apparatus, the turret assembly comprising:
  (a) a first shell with a plurality of first openings arranged in a substantially circular pattern around a first central axis, said first openings being of a size sufficient for a vial to pass therethrough;
  (b) a second shell with a second opening centered on a second central axis and a plurality of third openings arranged in a substantially circular pattern around said second central axis, each of said plurality of third openings being of a size insufficient for a vial to pass therethrough but large enough to permit passage of a transport means therethrough;
  (c) a plurality of elongated vial sleeves;
  (d) means for securing said first and second shells to each other and to said vial sleeves such that said first axis and said second axis are coincident, and such that each vial sleeve is aligned with a first opening in said first shell and a third opening in said second shell to form a plurality of holding assemblies for the plurality of vials;
  (e) a disk shaped baffle centrally disposed within the turret assembly, said baffle being disposed substantially perpendicular to said first and second central axes and having a substantially circular fourth opening centrally located in said baffle, said fourth opening being centered on said first and second central axes; and
  (f) a slider tube having a first end inserted through said fourth opening in said baffle and a second end having a base portion, said slider tube having an outer diameter substantially the same as the diameter of said fourth opening to allow said slider tube substantially free movement within said fourth opening, said first end having a groove disposed on its outer surface to accept a snap ring to retain the slider tube in said fourth opening.

10. The removable turret assembly of claim 9, further comprising:
  (g) a foam donut disposed between said base portion of said slider tube and said baffle.

* * * * *